United States Patent [19]

Hallmark

[11] 4,009,519
[45] Mar. 1, 1977

[54] ADJUSTABLE DISTAL EXTENSION HINGED STRESS BREAKER

[76] Inventor: Ralph Hallmark, 2 Brick Yard Drive R.R 1, Hudson, N.H. 03051

[22] Filed: July 23, 1975

[21] Appl. No.: 598,416

[52] U.S. Cl. .................................................. 32/5
[51] Int. Cl.² ....................................... A61C 13/22
[58] Field of Search .............................. 32/5, 6, 7

[56] References Cited

UNITED STATES PATENTS

| 2,797,456 | 7/1957 | Zahn | 32/5 |
| 2,797,482 | 7/1957 | Zahn | 32/5 |

*Primary Examiner*—Robert Peshock
*Attorney, Agent, or Firm*—Richard L. Miller

[57] ABSTRACT

A distal extension hinged stress breaker for a dental appliance which prevents lateral movement of the hinge. A shank portion is pivotally coupled to a head portion at one end thereof and a rear portion covers the opposite end thereof. The head portion is adapted to be coupled to an attachment for existing teeth, while the rear portion is adapted to be coupled to a case which fits over the mouth ridges and supports artificial teeth. The head portion includes free ends which can be distorted to provide a tight fit against the shank portion and prevent lateral movement of the shank portion with respect to the head portion.

7 Claims, 7 Drawing Figures

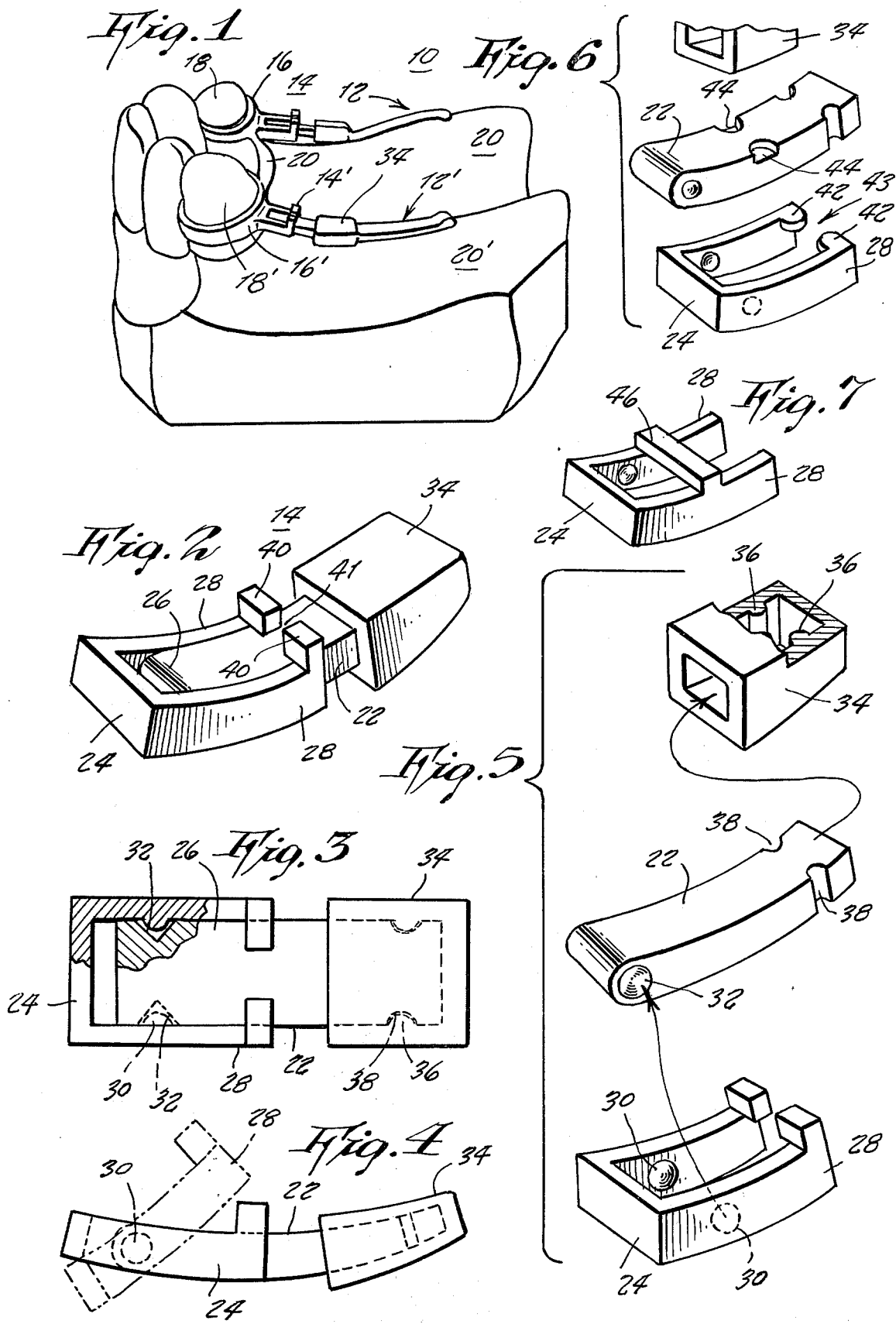

ADJUSTABLE DISTAL EXTENSION HINGED STRESS BREAKER

BACKGROUND OF THE INVENTION

1. Field of the Invention

This invention relates to dental applicances and more particularly to an improved hinge used in the formation of a denture prosthesis.

2. Description of the Prior Art

The use of artificial teeth as substitutes for missing natural teeth dates back to many generations. However, in recent times, this field of dentistry has become extremely sophisticated and provides various prosthesis which can substitute for partial groups of missing teeth or entire replacement of all missing teeth. The use of dental applicances for providing such prosthesis has become very complex and costly. Dental bridges are made in many shapes and forms for attachment to various parts of the mouth and tissue areas. The artificial teeth themselves are formed of various substances such as porcelain, plastic, etc.

In providing a partial denture prosthesis, it is necessary to connect the artificial teeth to the existing natural teeth and to retain them in a fixed position on the mouth ridges and tissues. The artifical teeth are usually placed on a plastic support which resembles the natural gums. The support is then fixed onto a metallic base which sits on the ridges of the mouth, such as the back gums. An abutment attachment is then placed onto the natural teeth. Such attachments can be flexible metal bands, clasps, or other means of attachment. It is then necessary to interconnect the abutment attachment to the metallic base holding the artificial teeth. Such interconnection is achieved by means of a hinge. The hinge not only provide a coupling between the abuttment attachment and the base member holding the artificial teeth, but also permits rotational motion of the two hinged parts to permit proper adjustment of the artificial teeth in the mouth.

In adjusting the artificial teeth during its fabrication, the dentist must frequently bend and turn the dental appliance. During such manipulation, however, the hinge becomes loose permiting lateral movement of the hinge. Such lateral movement, although slight, will subsequently produce a disturbance and inconvenience in the mouth of the user.

The mouth is generally extremely sensitive and any slight lateral movement of the artificial teeth provides great discomfort to the user. Even if the dental applicance is constructed without such lateral movement, when placing it in the mouth and providing the final adjustment there can again be introduced lateral movement to the hinge which will again provide discomfort and pain.

It is accordingly an object of the present invention to provide a distal extension hinged stress breaker which avoids the aforementioned problems of prior art devices.

Another object of the present invention is to provide an improved hinge for use in a dental applicance which can be adjusted to prevent lateral movement.

Yet a further object of the present invention is to provide a hinged stress breaker for a dental applicance which interconnects the abutment attachment with the base supporting the artificial teeth and wherein the hinge can provide rotational movement but prevents lateral movement.

A further object of the present invention is to provide a distal extension hinged stress breaker for a dental appliance, which can be easily adjusted both during construction thereof as well as in fitting thereof, to correct any lateral movement that may have been introduced.

Still a further object of the present invention is to provides a hinged stress breaker for a dental applicance which permits easy fitting of the dental appliance into the mouth and brings about an accurate fit giving comfort to the user.

These and other objects, features and advantages of the invention will, in part, be pointed out with particularity, and will, in part, become obvious from the following description of the invention, taken in conjunction with the accompanying drawings which form an integral part thereof.

SUMMARY OF THE INVENTION

Briefly, the invention provides a distal extension hinged stress breaker for a dental appliance including a head portion which is adapted to be coupled to an attachment connecting onto existing teeth. A longitudinal shank portion is pivotally coupled to the head portion by a pivot means which permits rotational movement between the shank portion and the head portion. A rear portion encloses the opposite end of the shank portion and is adapted to be coupled to a base which fits over the mouth ridges and supports the artificial teeth. A retention means extends from the head portion and holds the shank portion, preventing any lateral movement of the shank portion with respect to the head portion.

The retention means is provided by having the head portion extend into free deformable ends which abut the shank portion and hold it in a tight fit preventing lateral movement. Stop means are provided, for restricting the rotational movement to only one direction from an initial rest position.

BRIEF DESCRIPTION OF THE DRAWINGS

In the Drawings:

FIG. 1 is a perspective view of the hinged stress breaker of the present invention included with a dental restoration construction using various dental appliances;

FIG. 2 is a perspective view of one embodiment of the present invention;

FIG. 3 is a top view, partially cut away, of the embodiment shown in FIG. 2;

FIG. 4 is a side view of the embodiment shown in FIG. 2, and showing the rotational movement of the various portions;

FIG. 5 is an exploded perspective view of the various components forming the embodiment shown in FIG. 2;

FIG. 6 is an exploded perspective view showing a modified construction of the present invention, and FIG. 7 is a perspective view of still another modified design of one portion of the device of the present invention.

DESCRIPTION OF THE PREFERRED EMBODIMENTS

Referring now to FIG. 1 there is shown a dental restoration construction which has been placed in a mouth shown generally at 10 to replace a number of teeth that have been removed. The construction includes a dental appliance having a base member 12 connected to a hinge shown generally at 14 which in turn is coupled to an abutment attachment 16. The attachment is shown as a metal band or clasp which encircles the adjacent natural tooth 18 and is held in place thereby. A second similar appliance is shown having a base 12' connected through a hinge 14' to an attachment hook 16'. The two appliances are interconnected by means of a tetal bridge 20. The base members 12, 12' are positioned on the mouth ridges including the gums 20, 20'. Artificial teeth (not shown) would be typically held by plastic molds and placed on top of the base members 12, 12'.

The purpose of the hinge 14 is to transfer from the abutment teeth 18 to the gums 20 most of the masticating forces created while eating or chewing. The hinge therefore serves not only as a coupling member between the base and the attachment hook, but also serves as a stress breaker permitting rotational movement between the base member 12 and the attachment hook 16.

Referring now to FIGS. 2–5, there is seen that the hinge 14 includes a shank portion 22 which is a longitudinal member having a slight curvature thereto. A head portion 24 is pivotally coupled to one end 26 of the shank portion. The head portion 24 is of U-shaped construction and also has a slight curvature thereto to match the curvature of the shank portion. The ends of the U-shape head portion 28 are free without any rigid support interconnecting the two ends.

The head member 24 is coupled to the shank portion by means of the pivot arrangement. The pivot includes projections 30 on the inside of the U-shaped head portion and mating recesses 32 on the outer sides of the shank portion, whereby the projections can fit within the recesses providing a pivotal arrangement. The pivot permits rotation between the shank portion and the head portion as shown in FIG. 4.

A rear portion 34 encloses the opposite end of the shank portion and is rigidly secured onto the shank by means of a holding device. The holding device is shown to include protruding ridges 36 on the inner walls of the rear member which engage mating semi-cylindrical recesses 38 positioned on the sides of the shank member 22.

The head portion 24 is adapted to be coupled to the attachment hook 16 (FIG. 1) while the rear portion 34 is adapted to be interconnected to the base member 12 (FIG. 1).

A stop means is positioned on the head portion 24 to restrict the rotation of the shank with respect to the head portion such that rotation can only be had in one direction from an initial rest position. In FIGS. 2 - 5 such stop means include the arms 40 coupled to the ends 28. The arms 40 face towards each other but do not meet, leaving a space 41 between the two arms. The arms are positioned to lie above the surface of the shank portion. The arms prevent the shank from pivoting upward but only permits the shank to pivot downward with respect to the head, or alternately for the head to pivot upward with respect to the shank. Such rotation is shown in FIG. 4 where the head portion 24 is shown in phantom in its upward rotated position with respect to the shank 22.

Referring now to FIG. 6, there is shown an alternate embodiment for the stop portion. In FIG. 6, wherein like numerals represent like parts, the stop means includes the arms 42 which extend inwardly towards each other from the ends 28 of the head means 24. Again the arms do not meet but provide a space therebetween 43. However, in this embodiment the arms do not extend upwardly from the surface of the head means, but lie in the same plane as the surface of the head means. As a result, a portion of the arms extend downwardly. To accommodate such downward extending portions, recesses 44 are provided in the upper surface of the shank portion 22. Again, the stop means will prevent the rotation of the shank portion with respect to the head portion from being in both directions from a rest position, but will restrict it to only a single direction from an initial rest position.

FIG. 7 shows an alternate embodiment for providing the stop means, namely, a rigid strip 46 laterally extending across the legs of the U-shaped members. However, it is noted that the rigid strip does not connect the two ends of the head means but rather is spaced from the ends thereby permitting the two ends to again remain free to move.

It is therefore evident, that regardless of which type of stop means are utilized, there is always provided free ends extending from the head means which can be bent and deformed. In the embodiments shown in FIGS. 2 and 6, the ends are free because of the space provided between the two stop means. In the embodiment shown in FIG. 7 the ends are free because the stop means is spaced from the ends, leaving the ends free to be deformed.

Since the ends of the head means abut the sides of the shank portion and extend almost the entire length of the shank portion, they can tightly grasp the shank portion and prevent the shank portion from lateral movement with respect to the head portion. This, therefore, will prevent the lateral movement of the base member 12, connected to the rear portion 34 of the hinge with respect to the attachment hook 16 which is connected to the head portion.

During the construction of the dental appliance if the appliance is mishandled or readjusted, the intimate relationship between the head and the shank portions will be altered so as to cause lateral movement of these two ports. By deforming the free ends to provide a tight fit against the sides of the shank, such lateral movement can be corrected.

During the construction of the dental appliance, the lateral movement can be corrected as follows. The hinge head is rotated upward, as shown in phantom in FIG. 4, with respect to the shank portion. The two freely deformable ends 28 are squeezed together with a tool, such as a pair of pliers. This will bring the two arms slightly towards each other. When the arms and the head portion are again returned to the rest position, there will be a tight fit between the head and the shank, removing any lateral movement therebetween.

It is also possible to remove the undesirable lateral movement that may develop after the dental appliance has already been in use within the mouth of the wearer. To correct such lateral movement the dentist would approach the area of the hinge from the tissue side. Sufficient material would be removed from the immediate area of the free arms. The hinge is then moved to its active position, as shown in FIG. 4, with the head rotated upwards. An appropriate dental instrument is inserted and each of the arms are slightly moved inwardly. The hinge is then returned to its resting position and tested to be sure that the lateral movement has been removed. The procedure may be performed on both sides to bend both arms. The process may be repeated a number of times until proper adjustment is achieved. The material removed from the appliance may be replaced in a manner well known to dentists and technicians.

It is therefore seen that the present distal extension hinged stress breaker provides a coupling between parts of the dental appliance and also provides the necessary rotation needed for the dental appliance. However, by means of the free deformable ends of the head portion with respect to the shank portion, lateral movement of the hinge is prevented, thereby providing more comfort to the user and an improved dental reconstruction.

There has been disclosed heretofore the best embodiment of the invention presently contemplated. However, it is to be understood that various changes and modifications may be made thereto without departing from the spirit of the invention.

What is claimed is:

1. A distal extension hinged stress breaker for a dental appliance comprising;
   a. a head portion adapted to be coupled to an attachment which connects onto existing teeth;
   b. a substantially longitudinal shank portion;
   c. pivot means pivotally coupling one end of said shank portion to said head portion to permit rotational movement therebetween;
   d. a rear portion enclosing the opposite end of said shank portion and adapted to be coupled to a base which fits over the mouth ridges and support artificial teeth; and
   e. retention means extending from said head means and holding said shank means for preventing lateral movement of the shank means with respect to the head means,
   f. wherein said head portion is a U-shaped member and said retention means are free deformable ends extending from said head portion,
   g. further comprising stop means positioned on said head portion for restricting said rotational movement to only one direction from an initial rest position,
   h. and wherein said stop means includes arms coupled to the ends of said extensions and facing towards each other with a space therebetween, said arms positioned to lie above said shank portion.

2. A distal extension hinged stress breaker for a dental appliance comprising;
   a. a head portion adapted to be coupled to an attachment which connects onto existing teeth;
   b. a substantially longitudinal shank portion;
   c. pivot means pivotally coupling one end of said shank portion to said head portion to permit rotational movement therebetween;
   d. a rear portion enclosing the opposite end of said shank portion and adapted to be coupled to a base which fits over the mouth ridges and support artificial teeth; and
   e. retention means extending from said head means and holding said shank means for preventing lateral movement of the shank means with respect to the head means,
   f. wherein said head portion is U-shaped member and said retention means are free deformable ends extending from said head portion,
   g. further comprising stop means positioned on said head portion for restricting said rotational movement to only one direction from an initial rest position,
   h. and wherein said stop means includes arms coupled to the ends of said extensions and facing towards each other with a space therebetween, said arms positioned to lie in the same plane as the upper surface of the U-shaped member, and wherein said shank portion further comprises recesses in the top thereof to accommodate said arms.

3. The device as in claim 1 and wherein said retention means are extensions of the legs of said U-shaped member, said retention means lying parallel to the sides of said shank portion and extending the great part of the length of said shank portion, thereby forming a butting relationship with the sides of said shank portion.

4. The device as in claim 3 and wherein said shank portion and said head portion and said rear portion form a continuous curve.

5. The device as in claim 1 and wherein said stop means is a rigid strip laterally extending across the legs of said U-shaped member and spaced from the free deformable ends.

6. The device as in claim 1 and wherein said pivot means comprise, laterally extending projection means and mating recess means, one of said last two mentioned means being positioned in said head portion.

7. The device as in claim 1 and wherein said stress breaker is constructed of deformable metal.

* * * * *